United States Patent [19]
de Groot et al.

[11] Patent Number: 4,766,907
[45] Date of Patent: Aug. 30, 1988

[54] APPARATUS AND METHOD FOR PERFORMING A BIOPSY AND A DEVICE FOR MANIPULATING SAME

[76] Inventors: William J. de Groot, #1 Cedar Lawn South, Galveston, Tex. 77550; Theodore J. de Groot, 53 Lafayette St., Norwich, Conn. 06360; Joseph B. de Groot, 50 Morahapa Rd., Centerport, L. I., N.Y. 11721

[21] Appl. No.: 918,927

[22] Filed: Oct. 15, 1986

[51] Int. Cl.⁴ ............................................. A61B 10/00
[52] U.S. Cl. ....................................................... 128/754
[58] Field of Search ................ 128/314, 315, 749–758; 604/21, 51, 164, 264

[56] References Cited
U.S. PATENT DOCUMENTS

| | | | |
|---|---|---|---|
| 1,867,624 | 7/1932 | Hoffman | 128/754 |
| 2,839,049 | 6/1958 | McLean | 128/756 |
| 3,477,423 | 11/1969 | Griffith | 128/754 |
| 4,230,123 | 10/1980 | Hawkins | 604/51 |
| 4,345,589 | 8/1982 | Hiltebrandt | 604/264 |
| 4,619,272 | 10/1986 | Zambelli | 128/753 |

FOREIGN PATENT DOCUMENTS

| | | | |
|---|---|---|---|
| 0010321 | 4/1980 | European Pat. Off. | 128/754 |
| 0031228 | 7/1981 | European Pat. Off. | 128/756 |
| 1267960 | 1/1961 | France | 128/754 |
| 187228 | 11/1966 | U.S.S.R. | 128/754 |
| 422414 | 3/1972 | U.S.S.R. | 128/754 |
| 0707576 | 1/1980 | U.S.S.R. | 128/754 |

OTHER PUBLICATIONS
"Biopsy Needles" Becton et al., Oct. 1974.

*Primary Examiner*—Max Hindenburg
*Attorney, Agent, or Firm*—Brady, O'Boyle & Gates

[57] ABSTRACT

A cell or tissue retrieving instrument is slidably mounted within the needle of a conventional "Skinny Needle" and is connected to the needle syringe piston. In use, the needle with the instrument enclosed therein is inserted inwardly into the patient's organ. The instrument is held fixed and the needle is moved outwardly to expose the instrument within the organ. The instrument retrieves cell or tissue from the organ while being pulled into the needle and the needle with the enclosed instrument is removed from the patient.

A device is also disclosed for manipulating the "Skinny Needle" and tissue retrieving instrument in the method of performing the biopsy.

9 Claims, 2 Drawing Sheets

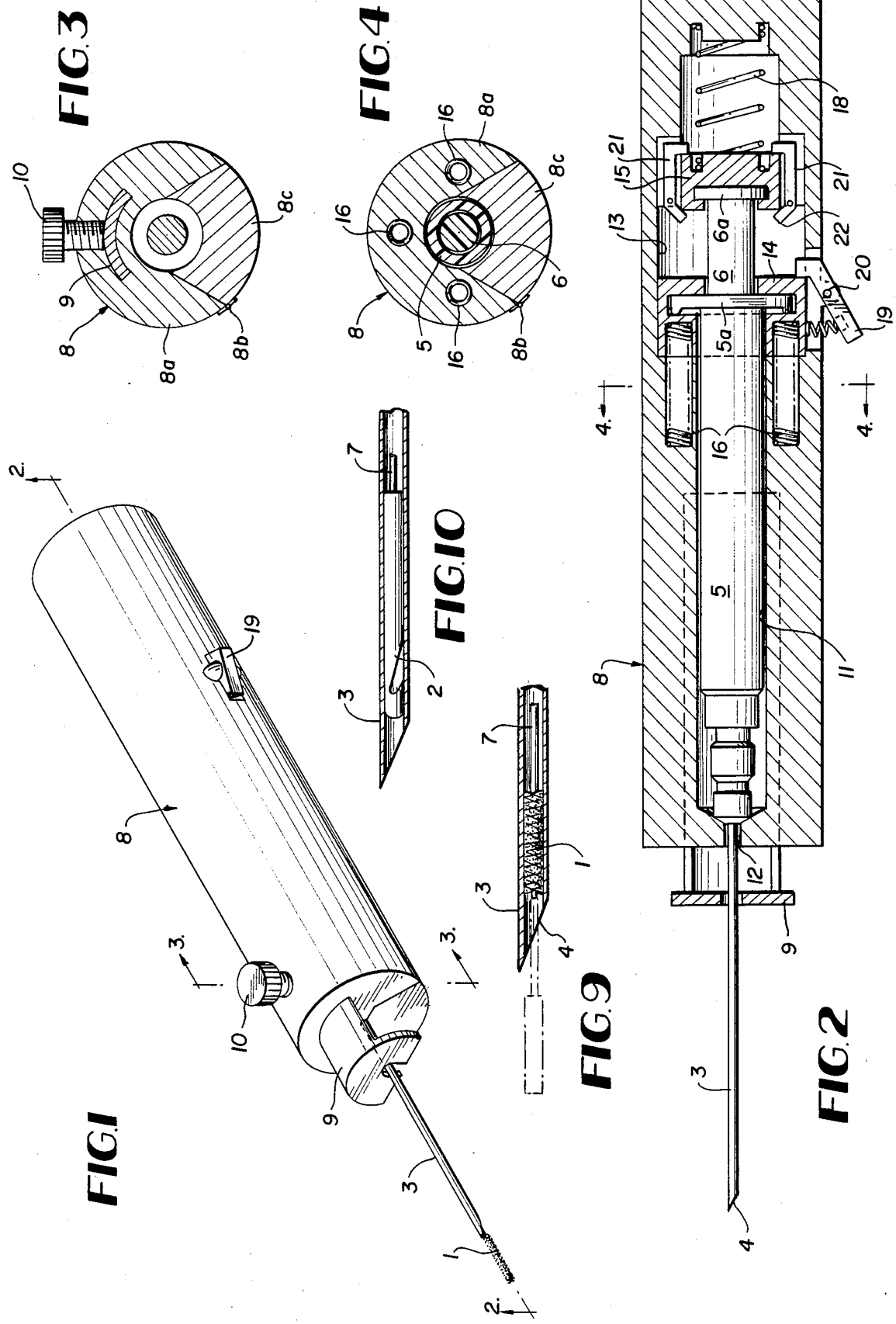

APPARATUS AND METHOD FOR PERFORMING A BIOPSY AND A DEVICE FOR MANIPULATING SAME

BACKGROUND OF THE INVENTION

The various organs in the human anatomy are subject to a variety of diseases which can only be diagnosed by cytologic or surgical pathologic examination of cells or tissue recovered by a biopsy procedure. Lung structure particularly presents unique problems with regard to the performance of a biopsy. The lung is enveloped in a thin membrane called the "pleura" which separates the lung from the inside of the chest wall which is similarly covered with a pleural membrane. A minute space called the "pleural space" is provided between the two membranes and if air is allowed to enter the pleural space, the lung will collapse, either partially or completely.

Efforts to biopsy the lung have focused on two requirements:

(1) The need to harvest cells or tissue from an organ which is mostly air, and (2) The need to obtain a biopsy specimen from within the lung substance without permitting air to leak either from the outside, or from the lung into the pleural space.

Two methods are commonly employed to biopsy the lung: namely, transbronchial wherein a flexible fiberoptic bronchoscope is employed as a conduit through which a biopsy instrument is passed from the outside of the patient through the airways of the lung into the lung tissue: and percutaneous wherein a biopsy needle is introduced through the chest wall usually after making a small skin incision.

While the transbronchial method is satisfactory as to a minimum of complications such as bleeding and lung collapse, the time, one to two hours, and expense in performing this procedure are quite formidable.

The percutaneous method has proven satisfactory as to time and expense; however, the various needles employed, such as the Silverman, Cope and Abrams, while providing relatively large pieces of tissue, produced a sizable injury to the pleural surface of the lung, thus causing a condition which promoted lung collapse. Furthermore, none of the needles was provided with an air seal, resulting in air being introduced from the outside causing the lung to collapse.

Currently, the only satisfactory procedure used for percutaneous lung biopsy is the "Skinny Needle" technique wherein a needle, similar to a standard intravenous needle (18 to 21 gauge) but somewhat longer and having an angled sharp cutting tip, is attached to a syringe. The needle is inserted into the lung through the chest wall and a vacuum is applied to the syringe whereby lung cells are sucked into the needle. The needle is then withdrawn from the chest and the cells forced from the needle onto a microscope slide for examination. This technique is simple since it can be performed frequently at the patient's bedside; it can be performed quickly, 15 to 30 minutes, and inexpensively. Since the needle is of narrow bore and has a sharp cutting tip, the injury to the pleural surface is minimal. This, together with the needle being air-sealed by the syringe, results in lung collapse being far less common than with any other percutaneous technique. The main disadvantage of the "Skinny Needle" technique, making it the least satisfactory of all techniques, is the relative paucity of the cellular material obtained because of the structure of the lung being predominantly air.

To overcome the disadvantage of the currently accepted and widely used "Skinny Needle" method of lung biopsy, and at the same time preserve its advantage in simplicity of use and low instances of complication, the apparatus of the present invention has been devised which comprises, essentially, a cell or tissue retrieving instrument, such as a transbronchial brush biopsy instrument or a Cope needle, slidably mounted within the needle of a conventional "Skinny Needle". The tissue retrieving instrument is connected to the needle syringe piston or plunger, whereby the "Skinny Needle" with the tissue retrieving instrument enclosed therein is inserted inwardly through the chest wall, visceral pleura and into the lung. The tissue retrieving instrument is held fixed and the "Skinny Needle" is moved outwardly to expose the tissue retrieving instrument within the lung. The instrument is then pulled into the "Skinny Needle" and the "Skinny Needle" is removed from the chest wall.

By the construction and arrangement of the apparatus of the present invention, cells are recovered, not by aspiration, but on the cell retrieving instrument, thus providing relatively large pieces of tissue. Since the assembly is air sealed, air leak from outside the chest is impossible, and because the cell retrieving instrument is introduced into the lung through a small cutting needle, pleural damage is no greater than experienced with the "Skinny Needle" technique.

In order to facilitate the manipulation of the "Skinny Needle" and associated cell retrieving instrument which would require a high degree of manual dexterity, and a considerable amount of training and practice, a device has been devised for controlling the sequence of the operation of withdrawing the "Skinny Needle" to expose the tissue retrieving instrument and then pulling the instrument into the needle, after the "Skinny Needle" is inserted into the tissue.

The device comprises, essentially, a housing adapted to receive the "Skinny Needle" and associated cell retrieving instrument. An adjustable gauge is mounted on the end of the housing to limit the depth of insertion of the "Skinny Needle" into the patient. A pair of latched, spring actuated, carriages are slidably mounted within the housing, one carriage being connected to the syringe barrel of the "Skinny Needle" and the other carriage being connected to the syringe plunger of the "Skinny Needle". By this construction and arrangement, the syringe barrel carriage is first released, causing the needle to move relative to the cell retrieving instrument. The syringe barrel then engages the latch of the syringe plunger carriage, to thereby release the plunger carriage, whereby the cell retrieving instrument is pulled into the needle.

BRIEF DESCRIPTION OF THE DRAWINGS

FIG. 1 is a perspective view of the device for manipulating the "Skinny Needle" and associated cell retrieving instrument of the present invention;

FIG. 2 is a sectional view taken along line 2—2 of FIG. 1;

FIG. 3 is a view taken along line 3—3 of FIG. 1;

FIG. 4 is a view taken along line 4—4 of FIG. 2;

FIG. 9 is a fragmentary sectional view illustrating the cell retrieving instrument as a transbronchial brush, the brush being shown in phantom extending outwardly relative to the needle and in solid lines the brush within the needle; and FIG. 10 is a fragmentary sectional view illustrating the cell retrieving instrument as a Cope needle.

DESCRIPTION OF THE PREFERRED EMBODIMENT

Figure 5:
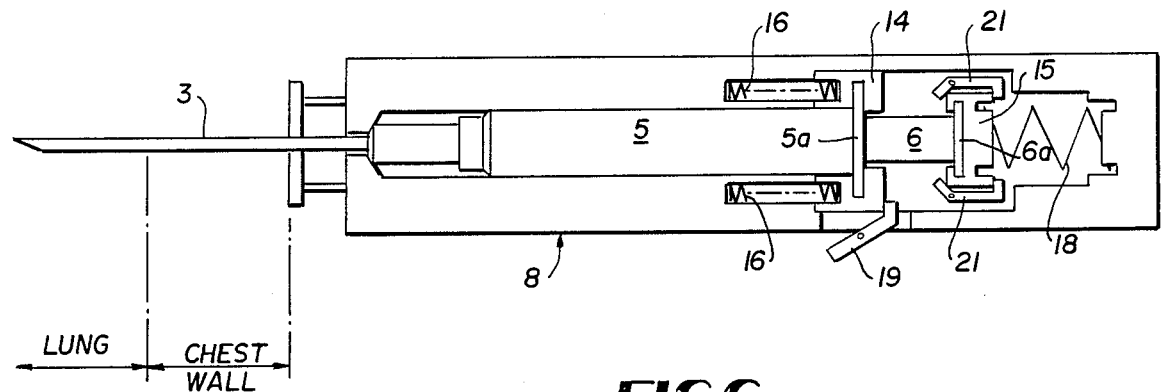
FIGS. 5, 6, 7 and 8 are schematic views of the method of performing a percutaneous lung biopsy employing the "Skinny Needle" and associated cell retrieving instrument of the present invention, and the operation of the device for manipulating the "Skinny Needle" and associated cell retrieving instrument.

Referring to the drawings, and more particularly to FIGS. 2, 9 and 10, the apparatus of the present invention for performing a percutaneous lung biopsy comprises, a cell or tissue retrieving instrument such as a transbronchial brush 1 (FIG. 9) or a Cope needle 2 (FIG. 10) slidably mounted within a needle 3 of a "Skinny Needle" assembly, the needle 3 being similar to a standard intravenous needle (18 to 21 gauge) but somewhat longer and having an angled sharp cutting tip 4. The needle 3 is rigidly connected to the end of a conventional syringe barrel 5 and the brush 1 or needle 2 is connected to the conventional syringe plunger 6 by a wire 7.

Figure 6:
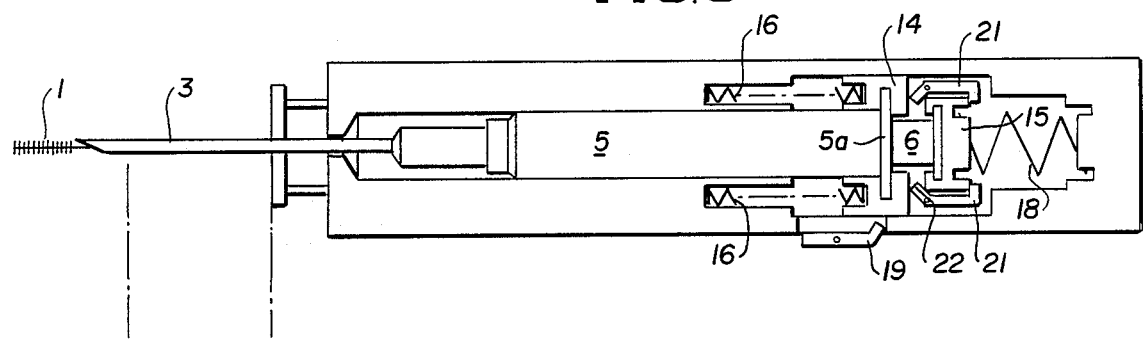
Figure 7:
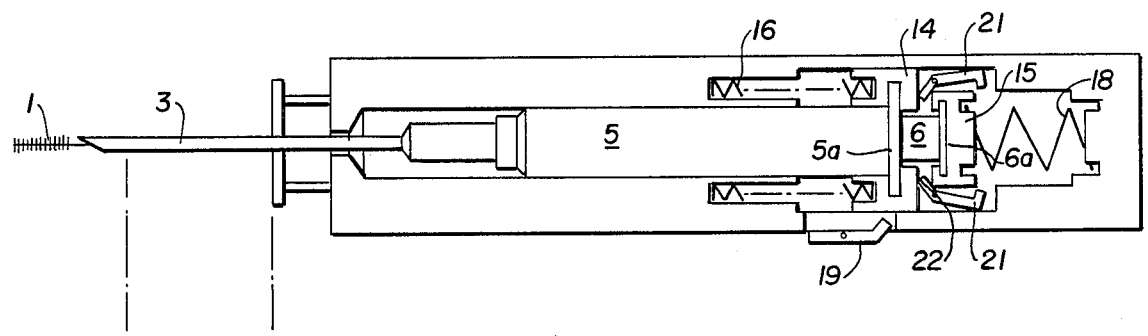
Figure 8:
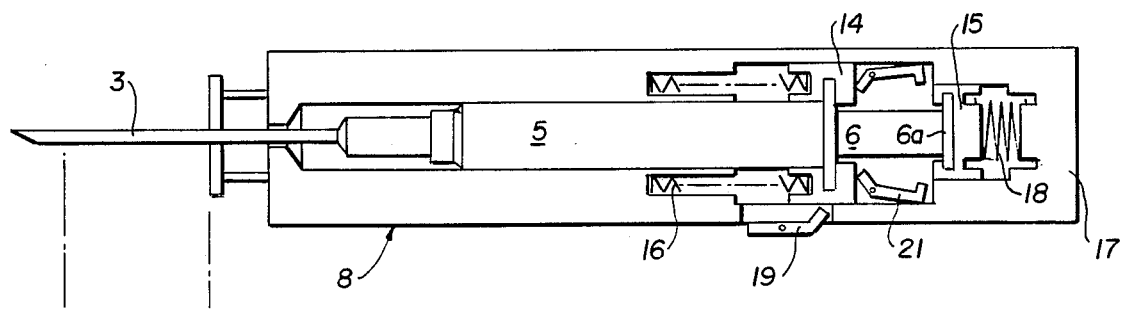

The method of the present invention of performing a percutaneous lung biopsy is illustrated in FIGS. 5 to 8, wherein the "Skinny Needle" assembly and associated transbronchial brush are inserted through the patient's chest wall into the lung, as shown in FIG. 5. The plunger 6 is held fixed while the barrel 5 is moved outwardly to thereby expose the brush 1 to the interior of the lung, as shown in FIG. 6. The barrel 5 is then held fixed and the plunger 6 is moved outwardly relative thereto to thereby pull or retract the brush 1 containing cellular tissue into the needle 3, as shown in FIGS. 7 and 8. This improved method reduces the number of steps previously employed in biopsy instruments wherein tissue removing instruments are insertable through the needles and then retracted therefrom. In the instant method, the tissue removing instrument 1 is carried by the needle 3 into the lung and the only movement of the brush 1 after it is positioned in the lung is its retraction into the needle.

The device for controlling the sequence of the operation of the present invention, as shown in FIGS. 5 to 8, is illustrated in FIGS. 1 to 4, wherein a housing 8 is provided with a flange member 9 slidably mounted in one end thereof and held in an adjusted position by a set screw 10 threadably mounted in the housing. The flange member 9 provides a gauge to limit the depth of insertion of the needle into the chest wall and lung of the patient as shown in FIG. 5. As will be seen in FIG. 2, the housing 8 is provided with a bore 11 for receiving the syringe barrel 5, the end of the housing having an aperture 12 communicating with the bore 11 through which the needle 3 extends. The opposite end of bore 11 communicates with a bore 13 of larger diameter in which a pair of carriages 14 and 15 are slidably mounted. The syringe barrel flange 5a is insertable into carriage 14 and the syringe plunger flange 6a is insertable into the carriage 15. A plurality of compression springs 16 are mounted within the housing and bias the carriage 14 in a direction toward the closed end 17 of the housing 8, and a tension spring 18 is mounted between the carriage 15 and the closed end 17 of the housing and is adapted to pull the carriage 15 toward the closed end of the housing. A spring-biased latch 19 is pivotally connected to the housing 8 as at 20 and is adapted to engage the carriage 14 and hold it against the biasing force of the springs 16. A pair of latches 21 are also pivotally connected to the housing for holding the carriage 15 against the tension force of the spring 18, the latches having finger portions 22 extending into the bore 13 and adapted to be engaged by the carriage 14 during the operation of the device, to be described more fully hereinafter.

To complete the structure of the device, as will be seen in FIGS. 3 and 4, the housing 8 consists of an upper portion 8a hingedly connected as at 8b to a lower or bottom portion 8c, whereby the housing may be opened for receiving the syringe assembly 5, 6, skinny needle 3 and associated cell retrieving instrument 1.

To use the device, the syringe assembly 3, 5 and 6 is placed in the housing 8 with the barrel flange 5a and plunger flange 6a inserted into their respective carriages 14 and 15. The carriages 14 and 15 are cocked by moving them against the biasing force of their respective springs 16 and 18 until engaged by their respective latches 19 and 21. The gauge member 9 is set in a predetermined position and the needle 3 is manually inserted through the chest wall into the lung until the gauge 9 engages the chest wall, as shown in FIG. 5. Latch member 19 is then manually actuated causing the carriage 14 to be biased outwardly in a direction toward the closed end of the housing, the syringe barrel flange 5a and associated syringe barrel 5 and needle 3 are also carried by the carriage 14 toward the closed end of the housing, as shown in FIG. 6. As the needle 3 moves outwardly, the brush 1 becomes exposed in the lung. Continued movement of the carriage 14 results in engagement with the fingers 22 of the latches 21, thereby releasing the carriage 15 as shown in FIG. 7. The carriage 15, through the tension force of spring 18, pulls the plunger flange 6a and associated plunger 6 and brush 1 toward the closed end 17 of the housing 8, to thereby pull the brush 1 into the needle 3. The assembly is then manually removed from the chest wall and the obtained specimens are removed from the brush for further examination.

While the apparatus, method and device of the present invention have been shown and described primarily for lung biopsy, it will be appreciated by those skilled in the art that the apparatus, method and device can also be used for the percutaneous biopsy of other organs.

It is to be understood that the form of the invention herewith shown and described is to be taken as a preferred example of the same, and that various changes in the shape, size and arrangement of parts may be resorted to, without departing from the spirit of the invention or scope of the subjoined claims.

We claim:

1. Apparatus for obtaining cells in performing a percutaneous biopsy comprising a relatively long, thin needle in the range of 18 to 21 gauge having an angled sharp cutting tip, a cell retrieving instrument slidably mounted in said needle, a syringe assembly connected to said needle and said cell retrieving instrument, said syringe assembly including a cylinder portion connected to one end of said needle, and a plunger portion slidably mounted in said cylinder portion, said cell retrieving instrument being connected to said plunger, whereby the needle and cell retrieving instrument can be slid relative to each other; a housing, said syringe assembly being removably mounted in said housing, said needle extending outwardly of said housing through a first end wall thereof, a pair of carriages slidably mounted in said housing, means connecting the syringe cylinder to one carriage, means connecting the syringe plunger to the other carriage, and means for sequentially sliding the syringe cylinder carriage and the syringe plunger carriage in a direction toward the other end of the housing, whereby the needle, with the cell retrieving instrument wholly contained therein, is manually inserted inwardly into a living body, the syringe cylinder carriage is first slid in a direction toward said other end of said housing, to thereby expose said cell retrieving instrument within the living body, and then the syringe plunger carriage is slid in a direction toward said other end of said housing to thereby pull said cell retrieving instrument back into said needle.

2. Apparatus as defined in claim 1, wherein the means for connecting the syringe cylinder and plunger to their respective carriage comprises a flange portion on the cylinder receivable into its carriage and a flange portion on the plunger receivable into its carriage.

3. Apparatus as defined in claim 1, wherein the means for sequentially sliding the carriages comprises spring means mounted in said housing and connected between said housing and the respective carriages for biasing the carriages in a direction toward the other end of said housing, and latch means operatively connected between said housing and said carriages for holding the carriages against the biasing force of said spring means.

4. Apparatus as defined in claim 1, wherein the housing includes an upper portion hingedly connected to a bottom portion, whereby the housing may be opened for receiving the syringe assembly.

5. Apparatus as defined in claim 1, wherein a flange member is adjustably mounted on the end wall of said housing, to thereby provide a gauge to limit the depth of insertion of the needle into the living body.

6. Apparatus as defined in claim 1 wherein the cell retrieving instrument comprises, a brush.

7. Apparatus as defined in claim 1, wherein the cell retrieving instrument comprises, a needle.

8. A method for obtaining cells in lung tissue while performing a percutaneous biopsy on a patient employing a relatively long, thin needle in the range of 18 to 21 gauge having an angled sharp cutting tip and a cell retrieving instrument slidably mounted in the needle comprising the steps of:
  (a) inserting the needle, with the cell retrieving instrument wholy contained therein, inwardly through the patient's chest into the lung;
  (b) maintaining the cell retrieving instrument fixed while sliding the needle outwardly relative thereto, to thereby expose the cell retrieving instrument within the patient's lung;
  (c) maintaining the needle fixed while sliding the cell retrieving instrument in an outward direction into the needle; and
  (d) removing the needle, the wholly contained instrument and retrieved cell from the patient's lung.

9. A method according to claim 8 in which the needle is connected to a syringe cylinder and the cell retrieving instrument is connected to a syringe plunger slidably mounted in the syringe cylinder wherein in step (b) the syringe plunger is held fixed while the syringe cylinder is moved relative thereto, and in step (c) the syringe cylinder is held fixed while the syringe plunger is moved relative thereto.

* * * * *